United States Patent
Degertekin et al.

(10) Patent No.: US 12,427,344 B2
(45) Date of Patent: Sep. 30, 2025

(54) MULTI-FUNCTIONAL SPARSE PHASED ARRAYS FOR GUIDING FOCUSED ULTRASOUND THERAPIES

(71) Applicant: Georgia Tech Research Corporation, Atlanta, GA (US)

(72) Inventors: Fahrettin Levent Degertekin, Atlanta, GA (US); Costas Arvanitis, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 185 days.

(21) Appl. No.: 18/007,562

(22) PCT Filed: Jun. 11, 2021

(86) PCT No.: PCT/US2021/036920
§ 371 (c)(1),
(2) Date: Dec. 1, 2022

(87) PCT Pub. No.: WO2021/252833
PCT Pub. Date: Dec. 16, 2021

(65) Prior Publication Data
US 2023/0211187 A1    Jul. 6, 2023

Related U.S. Application Data

(60) Provisional application No. 63/037,944, filed on Jun. 11, 2020.

(51) Int. Cl.
*A61N 7/00* (2006.01)
*A61B 8/00* (2006.01)
(Continued)

(52) U.S. Cl.
CPC .............. *A61N 7/00* (2013.01); *A61B 8/4494* (2013.01); *B06B 1/0292* (2013.01);
(Continued)

(58) Field of Classification Search
CPC .............. A61N 7/00; A61N 2007/0039; A61N 2007/0052; A61B 8/4494; A61B 8/5261;
(Continued)

(56) References Cited

U.S. PATENT DOCUMENTS

| | | | |
|---|---|---|---|
| 6,425,869 B1 * | 7/2002 | Rafter | A61B 8/4281 600/458 |
| 11,731,164 B2 * | 8/2023 | Ma | G01N 29/0654 367/137 |

(Continued)

FOREIGN PATENT DOCUMENTS

| | | |
|---|---|---|
| WO | 2018014021 A2 | 1/2018 |
| WO | 2018208942 A1 | 11/2018 |
| WO | 2019234497 A1 | 12/2019 |

OTHER PUBLICATIONS

International Search Report and Written Opinion from PCT Application No. PCT/US2021/036920 dated Nov. 12, 2021.
(Continued)

*Primary Examiner* — Dixomara Vargas
(74) *Attorney, Agent, or Firm* — TROUTMAN PEPPER LOCKE LLP; Ryan A. Schneider; Stephanie J. Remy

(57) ABSTRACT

Multifunctional ultrasound systems and methods for body section registration and mapping of microbubble dynamics. A system is provided that includes one or more micromachined ultrasonic transducer arrays (MUTAs) configured to capture a high-resolution image of at least a portion of a body section using ultrasound and monitor microbubble activity during ultrasound treatment. The system includes an image registration module configured to spatially register the high-resolution image with a reference image. The system includes electronics configured to control one or more of drive signal amplitude, frequency filtering, multiplexing, and DC bias voltage. The system can be configured to control ultrasound treatment based on the Monitoring
(Continued)

Verification monitoring of the microbubble activity during treatment.

27 Claims, 12 Drawing Sheets

(51) Int. Cl.
*B06B 1/02* (2006.01)
*G01S 7/52* (2006.01)
*G01S 15/89* (2006.01)

(52) U.S. Cl.
CPC ........ *G01S 7/5202* (2013.01); *G01S 7/52038* (2013.01); *G01S 15/8925* (2013.01); *G01S 15/8929* (2013.01); *G01S 15/899* (2013.01); *A61B 8/5261* (2013.01); *A61N 2007/0039* (2013.01); *A61N 2007/0052* (2013.01); *B06B 2201/76* (2013.01); *G01S 15/8927* (2013.01)

(58) Field of Classification Search
CPC .............. G01S 7/5202; G01S 7/52038; G01S 15/8927; G01S 15/8925; G01S 15/8929; G01S 15/899; B06B 1/0292; B06B 2201/76
See application file for complete search history.

(56) References Cited

U.S. PATENT DOCUMENTS

| | | | |
|---|---|---|---|
| 12,226,801 B2* | 2/2025 | Shelton | B06B 1/0651 |
| 2011/0178441 A1* | 7/2011 | Tyler | A61N 5/062 |
| | | | 601/2 |
| 2012/0058587 A1* | 3/2012 | Chang | B81C 1/00476 |
| | | | 257/E21.002 |
| 2015/0005756 A1 | 1/2015 | Tillander et al. | |
| 2015/0065922 A1 | 3/2015 | Kohler | |
| 2015/0105658 A1 | 4/2015 | Park et al. | |
| 2018/0325491 A1* | 11/2018 | Pekar | B06B 1/0292 |
| 2018/0372691 A1 | 12/2018 | Zhao et al. | |
| 2020/0064468 A1* | 2/2020 | Holbek | G01S 15/8993 |
| 2020/0164231 A1* | 5/2020 | Cannata | A61N 7/00 |
| 2020/0187910 A1* | 6/2020 | Pinton | A61B 8/085 |
| 2020/0229792 A1* | 7/2020 | Moshavegh | G01S 7/52039 |
| 2020/0254285 A1* | 8/2020 | Jang | A61B 8/4488 |
| 2020/0282055 A1* | 9/2020 | Barnsley | A61K 9/0009 |
| 2020/0338592 A1* | 10/2020 | Goericke | B06B 1/0629 |
| 2021/0204915 A1* | 7/2021 | Vortman | A61B 8/54 |
| 2022/0167944 A1* | 6/2022 | Matsumoto | A61B 8/4444 |
| 2022/0211350 A1* | 7/2022 | Pinton | G01S 15/899 |
| 2022/0401702 A1* | 12/2022 | Misener | A61B 5/6852 |
| 2023/0042741 A1* | 2/2023 | Rohling | G01N 29/2406 |
| 2023/0148869 A1* | 5/2023 | Zhao | B06B 1/0622 |
| | | | 600/407 |
| 2023/0149097 A1* | 5/2023 | Wentz | A61B 17/221 |
| | | | 600/424 |
| 2023/0255495 A1* | 8/2023 | Miller | G01N 29/0654 |
| | | | 600/407 |
| 2023/0340408 A1* | 10/2023 | Chalasani | C07K 14/195 |
| 2023/0380813 A1* | 11/2023 | Zhu | A61B 8/5261 |
| 2024/0091565 A1* | 3/2024 | Levy | A61N 7/02 |
| 2024/0099624 A1* | 3/2024 | Sutaria | A61B 5/02055 |
| 2024/0151838 A1* | 5/2024 | Brock | G01S 15/8993 |
| 2024/0225611 A1* | 7/2024 | Firouzi | A61B 5/4064 |
| 2024/0286171 A1* | 8/2024 | Bayram | B06B 1/0292 |

OTHER PUBLICATIONS

Supplemental European Search Report from Application No. 21821737.0 dated Jun. 17, 2024.

* cited by examiner

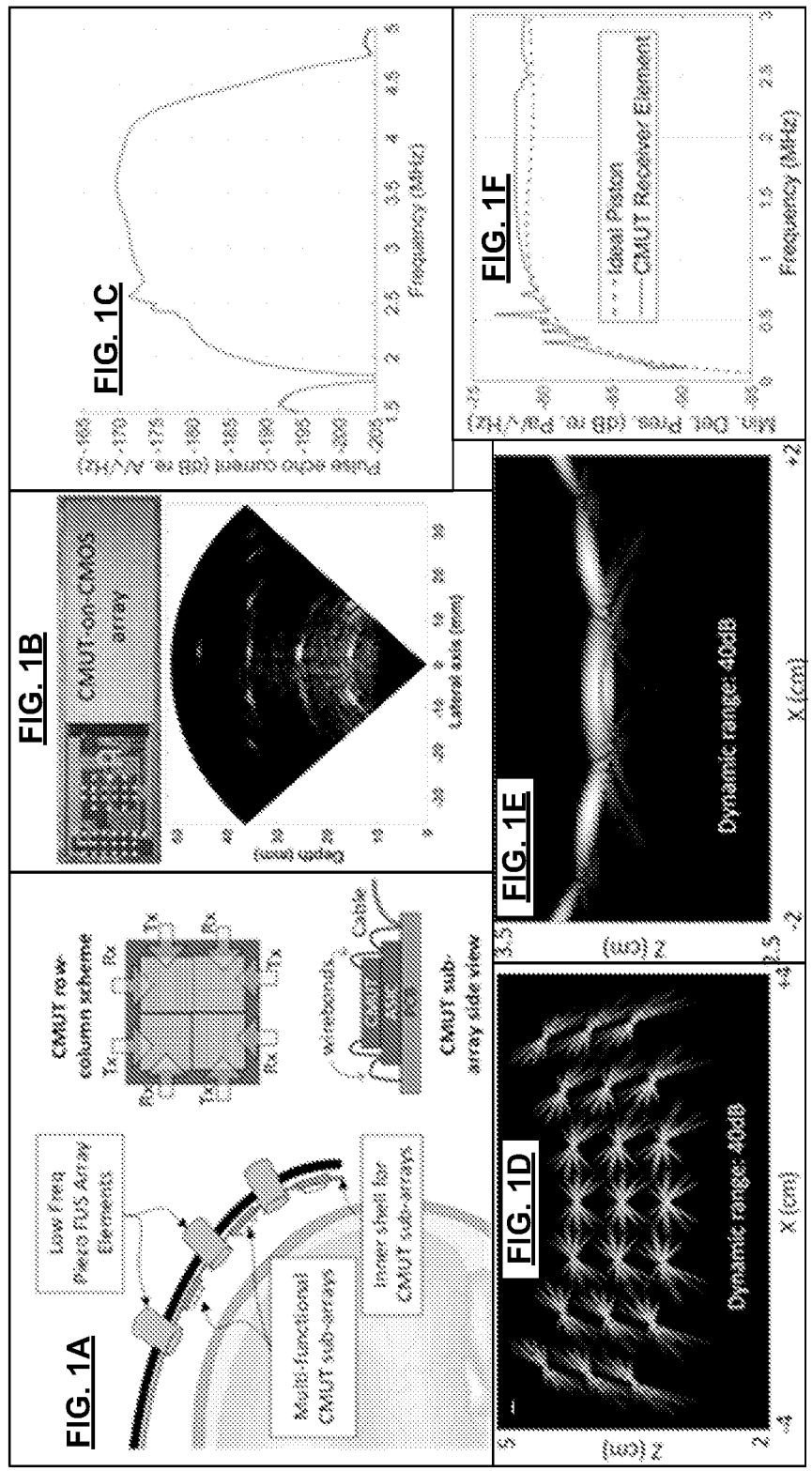

Capacitive micromachined ultrasound transducer (CMUT) structure

Ultrasound transmit mode

Ultrasound receive mode

MULTI-FUNCTIONAL SPARSE PHASED ARRAYS FOR GUIDING FOCUSED ULTRASOUND THERAPIES

CROSS-REFERENCE TO RELATED APPLICATION

This application claims priority to U.S. Provisional Patent Application Ser. No. 63/037,944, filed on 11 Jun. 2020, entitled: "Multi-Functional Sparse Phased Arrays for Guiding Focused Ultrasound Therapies," the contents of which are hereby incorporated by reference in their entirety as if presented herein in full.

STATEMENT REGARDING FEDERALLY SPONSORED RESEARCH OR DEVELOPMENT

This invention was made with government support under Award Nos. CA239039, EB02453 and EB016971 awarded by the National Institutes of Health. The government has certain rights in the invention.

FIELD

This disclosure generally relates to ultrasound-focused ultrasound (FUS) therapies using adaptable machined ultrasonic transducer arrays (MUTAs) for controlling FUS placement and emission energy.

BACKGROUND

Focused ultrasound (FUS) based therapies are being developed for a significant number of applications including drug delivery, fractionation of tissue, lysing of blood clots, amplifying circulating biomarkers, removal of amyloid plaque, and neuromodulation. These applications target various organs in the body, from the brain to the liver, prostate, and vasculature. Ensuring the safety and efficacy of these therapies require spatial and temporal assessment and quantification of the mechanical and thermal effects, ideally fast enough for real-time feedback control.

One mechanical effect of FUS application is the generation of microbubble oscillations, either instigated by exceeding the pressure threshold for spontaneous cavitation activity in the targeted tissue or seeded by intravenously administered lipid-stabilized gas pockets (or other shell materials), superheated droplets, or other particles. Such localized microbubble activity offers the ability to noninvasively focus mechanical energy at the cellular level for treatment purposes. However, sometimes this type of activity can be generated unintentionally at undesired locations due to microbubbles trapped in tissue or focusing errors caused by aberrations.

The type of oscillation leading to inertial or stable cavitation can determine the harmful/useful nature of the FUS application. Depending on the FUS-induced activity in the tissue and on microbubbles, different types of acoustic emissions are generated with harmonic, subharmonic, and broadband nature.

For accurate determination of FUS activity location, the aberration (and attenuation) due to the different types of media (tissues, fluids, bone, etc.,) over the path between the emission source and the receivers should be corrected, particularly for cases where FUS therapy is applied to the brain through the skull. Traditionally, imaging information obtained from computer tomography (CT) or magnetic resonance imaging (MRI) has been utilized to help aid FUS therapy localization and/or aberration correction, however, such methods can be expensive and restrictive. Accordingly, there is a need for improved systems and methods that can provide location registration with pre-op CT and/or MRI images. There is also a need for improved systems and methods that can detect broadband acoustic emissions from FUS applications in the body with high sensitivity and localization capability for safer FUS applications. Furthermore, there is a need for combining imaging (for location registration), broadband emission detection (for microbubble dynamics), and/or FUS therapy capabilities in the same apparatus. Embodiments of the present disclosure are directed to this and other considerations.

BRIEF SUMMARY

The disclosed technology includes adaptable machined ultrasonic transducer arrays (MUTAs) and methods for controlling FUS placement and emission energy.

Consistent with exemplary embodiments disclosed herein, a multifunctional ultrasound system is provided for body section registration and mapping of microbubble dynamics. The system includes one or more micromachined ultrasonic transducer arrays (MUTAs) configured to capture a high-resolution image of at least a portion of a body section using ultrasound and monitor microbubble activity during ultrasound treatment. The system includes an image registration module configured to spatially register the high-resolution image with a reference image. The system includes electronics configured to control one or more of drive signal amplitude, frequency filtering, multiplexing, and DC biasing.

Consistent with exemplary embodiments disclosed herein, a multifunctional ultrasound system is provided for body section registration, mapping of microbubble dynamics, and ultrasonic treatment. The system includes one or more micromachined ultrasonic transducer arrays (MUTAs) configured to capture a high-resolution image of at least a portion of a body section using ultrasound, monitor microbubble activity during ultrasound treatment, and generate focused ultrasound energy for treatment. The system includes an image registration module configured to spatially register the high-resolution image with a reference image. The system includes electronics configured to control one or more of drive signal amplitude, frequency filtering, multiplexing, and DC biasing. In certain implementations, the MUTAs can include one or more capacitive micromachined ultrasonic transducers (CMUTs). In certain implementations, the MUTAs can include one or more piezoelectric micromachined ultrasonic transducers (PMUTs).

Consistent with exemplary embodiments disclosed herein, a method is provided for body section image registration and mapping of microbubble dynamics. The method includes capturing, with ultrasound using one or more micromachined ultrasonic transducer arrays (MUTAs), a high-resolution image of at least a portion of a body section, spatially registering the high-resolution image to a reference image of the body section, monitoring microbubble activity during ultrasound treatment using image reconstruction, and combining one or more of output signals and captured images from the one or more MUTAs to form a composite image of the body section for one or more of image registration and treatment guidance.

Consistent with exemplary embodiments disclosed herein, a method is provided for body section image registration, ultrasonic treatment, and mapping of microbubble dynamics. The method includes capturing, with ultrasound using one or more micromachined ultrasonic transducer arrays (MUTAs), a high-resolution image of at least a portion of a body section, spatially registering the high-resolution image to a reference image of the body section, generating focused ultrasound energy for treatment, monitoring and controlling microbubble activity during ultrasound treatment using image reconstruction, and combining one or more of output signals and captured images from the one or more MUTAs to form a composite image of the body section for one or more of image registration and treatment guidance.

The capabilities of the systems and methods disclosed herein are amenable to closed-loop acoustic emission-based controllers for tuning exposure settings to attain prescribed microbubble activity, which may provide certain advantages for improving brain treatment accuracy and safety.

Further features of the disclosed design and the advantages offered thereby are explained in greater detail hereinafter regarding specific embodiments illustrated in the accompanying drawings, wherein like elements are indicated be like reference designators.

BRIEF DESCRIPTION OF THE DRAWINGS

Reference will now be made to the accompanying drawings, which are not necessarily drawn to scale, and which illustrate various implementations and aspects of the disclosed technology and, together with the description, serve to explain the principles of the disclosed technology.

FIG. 1A depicts CMUT arrays integrated with piezo-based focused ultrasound (FUS) elements over a 3D shell for transcranial FUS therapy and monitoring, per certain exemplary implementations of the disclosed technology.

FIG. 1B shows a CMUT-on-CMOS chip (top) with a phantom image (bottom), where the phantom image is detected using the CMUT-on-CMOS chip.

FIG. 1C shows a simulated pulse-echo response spectrum over an active imaging bandwidth of the CMUT-on-CMOS chip.

FIG. 1D depicts field II simulation results using 3 subarrays 3 cm away from a skull surface with a 12 cm ROC for point targets on a curved skull surface.

FIG. 1E depicts field II simulation results using 3 subarrays 3 cm away from a skull surface with a 12 cm ROC for point targets on curved skull surface with specular reflection.

FIG. 1F depicts curvature recovery and sub-mm resolution capabilities of the CMUT receiver. Calculated pressure noise levels for the ideal piston (dashed curve) are based on CMUT element dimensions of 2.8 mm×0.75 mm.

DETAILED DESCRIPTION

Figure 2A:
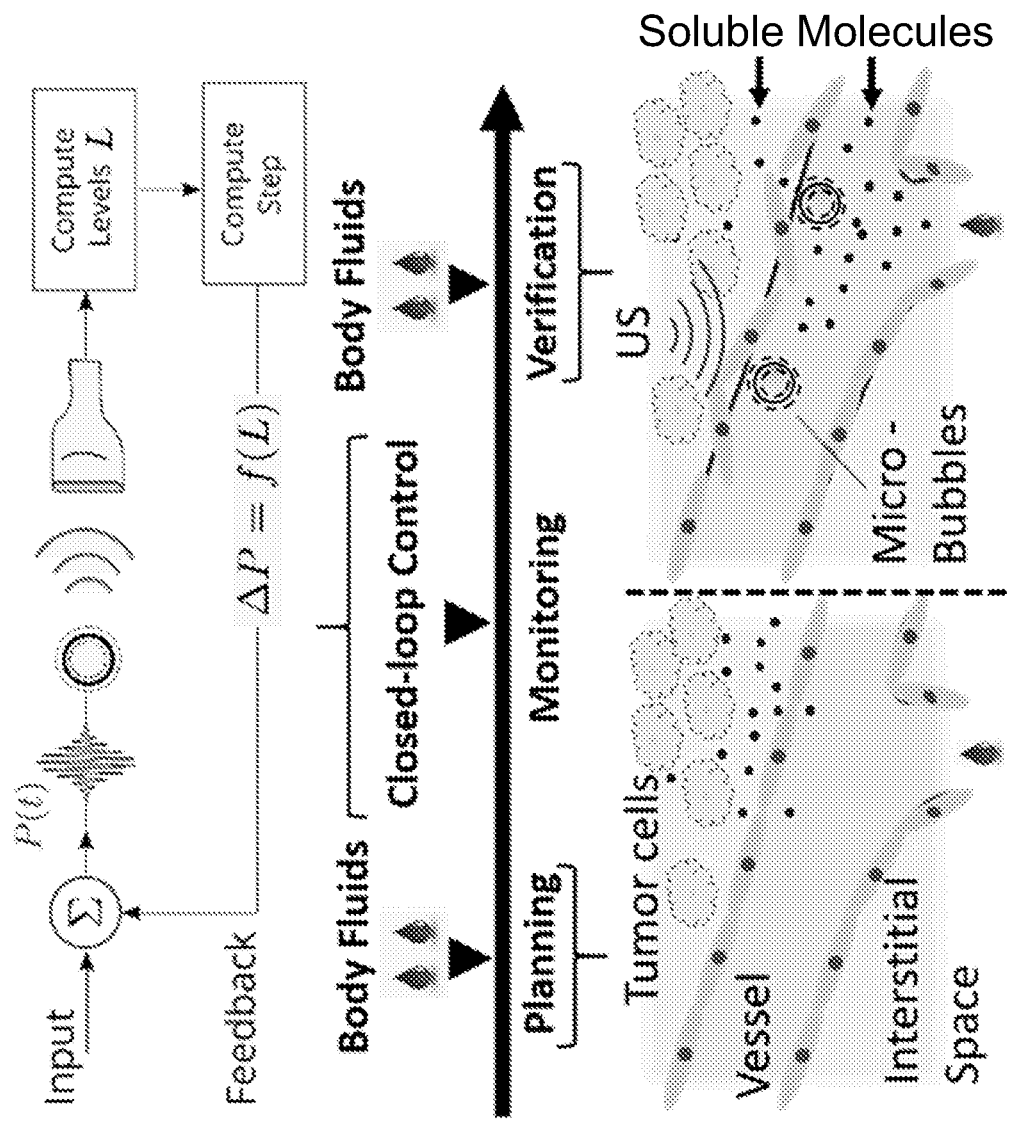
FIG. 2A depicts FUS therapy in which closed-loop ultrasonic (US) microbubble monitoring and image guidance may be utilized for planning, monitoring, and/or verification of FUS treatment.

Machined ultrasonic transducer (MUT) technology offers a range of desirable characteristics for treatment planning and monitoring of focused ultrasound (FUS) therapies. Capacitive machined ultrasonic transducers (CMUTs), in particular, can have high receive sensitivity and wide bandwidth, which can enable the detection of the weak microbubble acoustic emissions through the skull and/or other body tissues and fluids.

Certain exemplary implementations of the disclosed technology utilize machined ultrasonic transducer arrays (MUTAs) that can include CMUTs and/or piezo machined ultrasonic transducers (PMUTs). A benefit of using CMUTs for the MUTAs is that the vibrational mode(s) of the CMUTs can be adapted to frequencies of interest by adjusting a DC bias voltage across the electrodes. Following certain exemplary implementations of the disclosed technology, the DC bias can be adjusted to cause the CMUT to operate in non-collapsed mode, a collapsed mode, or a deep collapsed mode. Additional background information regarding electrode biasing may be found in Guldiken, R. et al. "CMUTS with dual electrode structure for improved transmit and receive performance." IEEE Transactions on Ultrasonics, Ferroelectrics and Frequency Control 53 (2006): 483-491, which is incorporated herein by reference as if presented in full.

In the non-collapsed mode, the membrane diaphragm of the CMUT can vibrate responsive to a received acoustic/ultrasonic field (for detection) and/or an applied AC voltage across the electrodes (for acoustic/ultrasonic field emission). In this non-collapsed mode, the CMUT diaphragm can operate analogously to a drumhead constrained at the edges. In certain exemplary implementations, an application of a small DC bias across the electrodes may cause a small variation in the associated frequency response due to electrostatic deflection of the associated diaphragm.

In certain exemplary implementations, the DC bias may be increased so that the top electrode/diaphragm is attracted towards the bottom electrode. According to an exemplary implementation of the disclosed technology, the CMUT may be configured so that upon application of a sufficient DC bias, a central portion of the diaphragm will make contact with the bottom portion of the CMUT, thereby constraining the diaphragm at both edges and the center. Such collapsed-mode operation has the effect of changing the resonance characteristics such that the associated frequency response of the CMUT may be increased since the effective fundamental vibrational mode has been changed due to the additional constraining point where the center of the diaphragm touches the bottom. This typically results in a significant increase in the frequency response compared to the non-collapsed state. Certain implementations of the disclosed technology may utilize such a biasing feature to select different modes of frequency operation for different purposes, as will be explained below.

Certain exemplary implementations of the disclosed technology may utilize an even greater DC biasing voltage to cause the CMUT to operate in a deep-collapsed mode, in which a region of contact (by the diaphragm with the bottom portion of the CMUT) may be increased with increasing biasing, thereby further changing the resonance characteristics of the diaphragm and (typically) increasing the resonant frequency and associated frequency response.

Certain implementations of the disclosed technology may utilize the non-collapsed, collapsed, and/or deep-constrained to change the effective operational response of the MUT device over a range from 100 kHz or lower for subharmonics, to 10s of MHz harmonics and all frequencies in between for broadband emission detection and/or ultrasonic therapy.

In certain exemplary implementations, the above-referenced mode control may be combined with low noise electronics to enable thermal-mechanical noise-limited detection. Certain exemplary implementations of the disclosed technology may utilize passive acoustic imaging (PAI) to provide a significant decrease in the threshold for the detection of microbubble acoustic emissions. Certain exemplary implementations of the disclosed technology may enable the sensitivity and safety margin of FUS therapy procedures to theoretical limits (single microbubble detection). Certain implementations may provide the ability to detect between 1 and 1000 microbubbles in an associated field of view.

Under certain exemplary implementations of the disclosed technology, large bandwidths (0.1-10 MHz) may be achieved using a CMUT with a single lateral size. In other implementations, thin membranes and/or CMUT arrays or elements can be formed by combining multiple membrane sizes, each covering a certain frequency band. In this case, signals picked up by these membranes may be combined into a single signal by electrically connecting the elements to form a single element, and/or by detecting and processing the signals with separate elements. In certain implementations, separate signals from separate elements may be combined using phase delays.

According to an exemplary implementation of the disclosed technology, silicon-based miniaturization and electronics integration may be utilized to provide subarrays with element spacing (down to $\lambda/2$ for the desired frequencies) while keeping the number of connecting cables at a manageable size. For example, 256 sub-arrays, each containing 32 elements can be managed with about 1000 micro-cables. In certain exemplary implementations, multiplexing may be utilized to reduce the count of the micro-cables, as will be discussed with respect to FIG. 2B. In some embodiments, these programmable adaptable MUTAs may be used in receive mode only to detect FUS-induced signals for passive imaging modes like PAL. In other implementations, the programmable adaptable arrays may be used in transmit/receive format for high-resolution active imaging of the skull (B-mode).

Certain exemplary implementations disclosed herein may enable high-resolution tracking of microbubble activity, which may further enable visualization of vascular biomarkers for independent targeting verification, as will be discussed below with respect to FIG. 2A.

Certain exemplary implementations of the disclosed technology may utilize machined ultrasonic transducer arrays MUTAs to enable precise registration of diagnostic MRI and/or pre-operative CT images, as will be discussed below with respect to FIG. 4. Certain implementations may utilize MRI-compatible MUTAs, such as CMUTs, where the device may be exposed to (or used during exposure to) strong electromagnetic fields.

In the following, several exemplary embodiments and/or use cases of the disclosed technology are discussed. Certain programmable, adaptable, broadband, and low noise subarray concepts for registration and/or guidance of FUS are described with a focus on transcranial FUS applications. However, these techniques and concepts are equally applicable for any number of FUS applications in which monitoring the tissue and microbubble response in the overall treatment are employed.

Referring now to the figures, exemplary embodiments of the disclosed technology are herein described. It is to be understood that the figures and descriptions of the disclosed technology have been simplified to illustrate elements that are relevant for a clear understanding, while eliminating, for purposes of clarity, other elements found in typical electronics circuits and associated devices. Those of ordinary skill in the art will recognize that other elements may be desirable and/or may be required to implement the disclosed technology. However, because such elements are well known in the art, and because they may not facilitate a better understanding, a discussion of such elements is not provided herein.

As depicted in FIG. 1A, and following certain exemplary implementations of the disclosed technology, CMUT technology may be utilized and/or combined with PMUT (piezoelectric) technology, particularly in FUS therapies below about 3 MHz, where certain CMUT devices may produce limited pressure output. In such exemplary implementations, high power therapeutic FUS may be generated using a transducer or transducer array made of piezo-ceramic transducers, while CMUT sub-arrays may provide broadband, low noise receive-only or higher frequency transmit/receive imaging capability. Per certain exemplary implementations of the disclosed technology, the outputs of such a CMUT sub-array system can be processed and used with different FUS control algorithms such as described in the PCT patent application publication WO2020097298 entitled "Systems and methods for ultrasound imaging and focusing," which is incorporated herein by reference as if presented in full.

By certain exemplary implementations of the disclosed technology, certain microbubble dynamics emissions can be processed using passive acoustic imaging (PAI), frequency or time domain beamforming, or other emerging beamforming techniques such as short lag spatial coherence. Certain implementations may be utilized to monitor such acoustic emissions with high sensitivity in the frequency range that characterizes the microbubble dynamics (e.g. type and strength) in the three-dimensional space.

As depicted in FIG. 1A (and FIG. 2A) certain exemplary implementations of the disclosed technology may utilize one or more MUTAs in FUS to open the blood-brain barrier (BBB) for drug delivery. In certain exemplary implementations, a CMUT multi-functional phased array may be used for ultrasound-guided FUS treatment planning and monitoring without intraoperative MRI. This embodiment enables high-resolution imaging of the skull and vascular biomarkers for accurate targeting verification along with PAI and control of FUS-BBB disruption through the human skull. In certain exemplary implementations, a CMUT array may be integrated over a 3D shell and overlaid with a low frequency (typically around 0.3 MHz) piezo ceramic-based sparse FUS phased array. In certain implementations, the two-shell structure with CMUT and PMUT subarrays may be utilized.

The inset diagrams in FIG. 1A depict example top- and side-views depictions of a Tx and Rx row-column array structure. The top-view inset diagram in FIG. 1A depicts a 2×2 subarray. Other exemplary implementations of the disclosed technology may utilize different sized subarrays, including but not limited to 4×4 subarrays, and/or up-to 10×10 subarrays.

FIG. 1B shows a CMUT-on-CMOS chip (top) with a phantom image (bottom), where the phantom image is detected using the CMUT-on-CMOS chip. FIG. 1C shows a simulated pulse-echo response spectrum over an active imaging bandwidth of the CMUT-on-CMOS chip. FIG. 1D depicts field II simulation results using 3 subarrays 3 cm away from a skull surface with a 12 cm ROC for point targets on a curved skull surface. FIG. 1E depicts field II simulation results using 3 subarrays 3 cm away from a skull surface with a 12 cm ROC for point targets on curved skull surface with specular reflection. FIG. 1F depicts curvature recovery and sub-mm resolution capabilities of the CMUT receiver. Calculated pressure noise level for the ideal piston (dashed curve in FIG. 1F) utilized element dimensions of 2.8 mm×0.75 mm element for reasonable computation time. In certain implementations, scaling may be utilized to improve the signal-to-noise ratio (SNR). In certain implementations, two or more MUTAs may be selectively connected using on-chip switches to provide a larger effective detection area. In certain exemplary implementations, signals from individual MUTAs may be combined or processed with signals from adjacent MUTA to improve SNR. For example, scaling to a 40 square mm area may results in 20 dB SNR for 0.03 Pa. In certain implementations, CMUT elements may be utilized that are 78 μm square with 200 nm gap. Other element sizes, shapes, spacings, and gaps may be utilized without departing from the scope of the disclosed technology.

FIG. 2A depicts FUS therapy in which closed-loop ultrasonic (US) microbubble monitoring and image guidance may be utilized. The disclosed technology may be utilized for planning, monitoring, and/or verification of FUS treatment. In this example, tumor-soluble molecular reporters may be utilized to aid FUS drug delivery.

FIG. 2A depicts FUS therapy in which closed-loop ultrasonic (US) microbubble monitoring and image guidance may be utilized for planning, monitoring, and/or verification of FUS treatment.

Figure 2B:
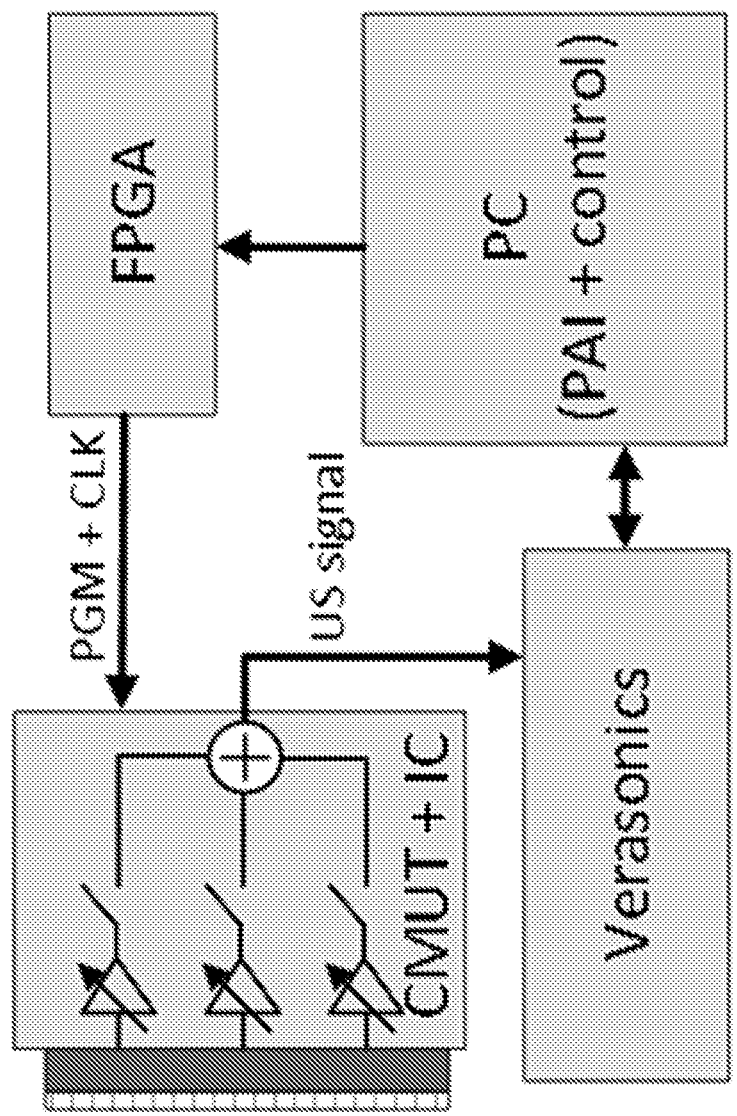
FIG. 2B is an illustration of a schematic block diagram for interfacing one CMUT element with a PAI controller.

FIG. 2B is an illustration of a schematic block diagram for interfacing one CMUT element with a PAI controller.

Figure 2C:
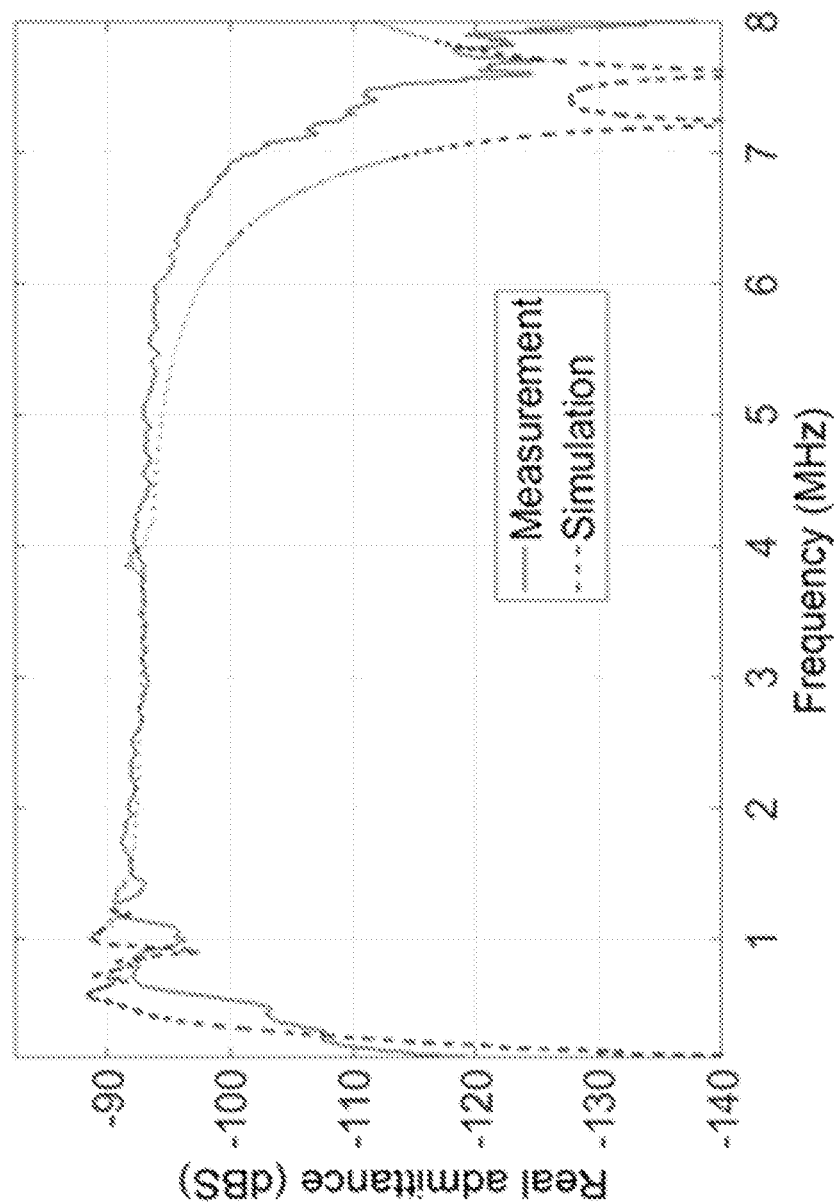
FIG. 2C depicts simulated (dashed curve) and measured (solid curve) CMUT admittance.

FIG. 2C depicts simulated (dashed curve) and measured (solid curve) CMUT admittance.

Figure 2D:
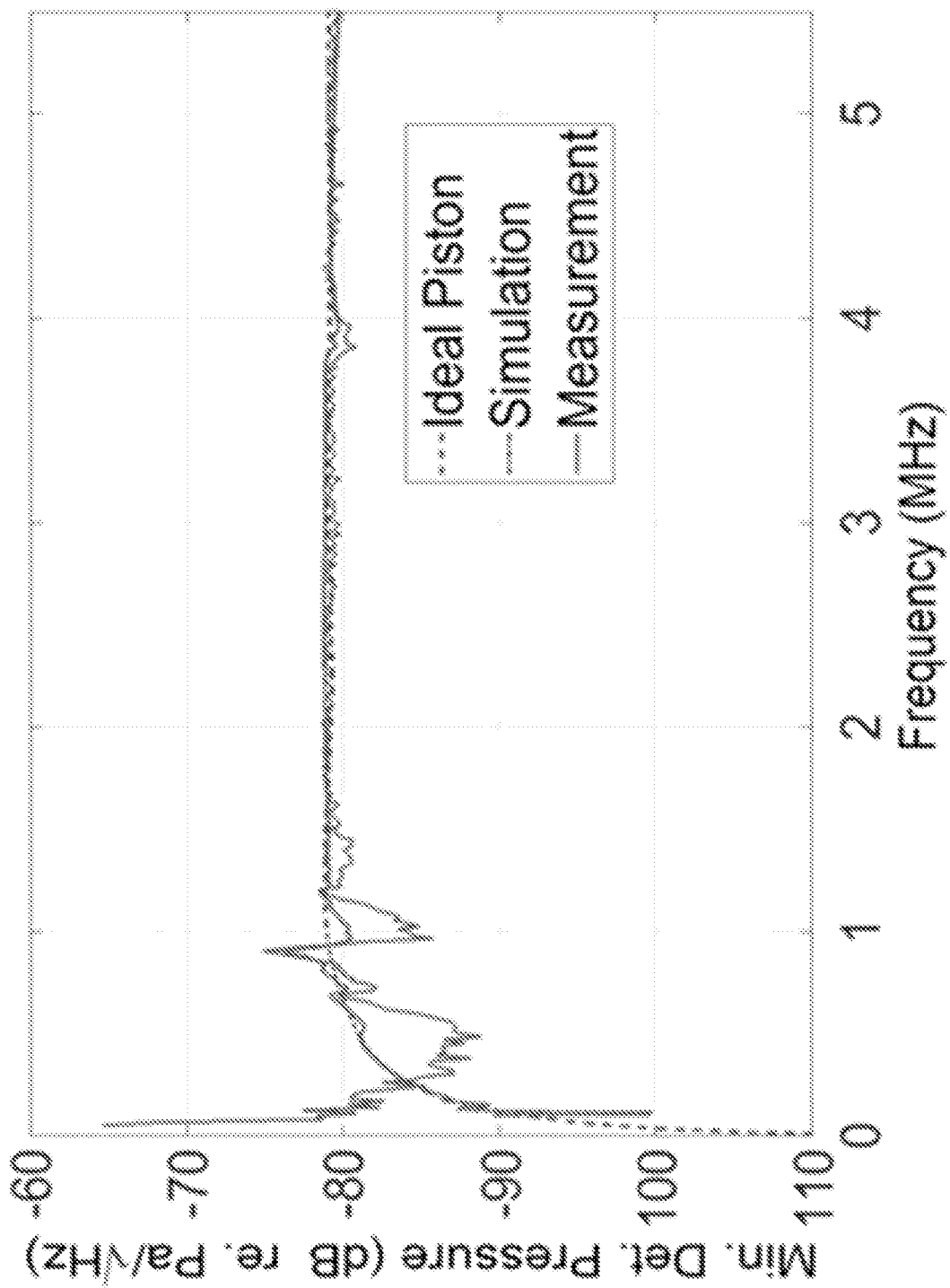
FIG. 2D depicts CMUT element ideal (dotted curve), simulated (dashed curve), and measured (solid curve) pressure noise levels for a 2.8 mm×0.75 mm element. In this example, the CMUT membranes are 78 μm square with a 200 nm gap.

FIG. 2D depicts CMUT element ideal (dotted curve), simulated (dashed curve), and measured (solid curve) pressure noise levels for a 2.8 mm×0.75 mm element. In this example, the CMUT membranes are 78 μm square with a 200 nm gap. Pressure noise level for 2.8 mm×0.75 mm element (used for reasonable computation time).

Figure 3A:
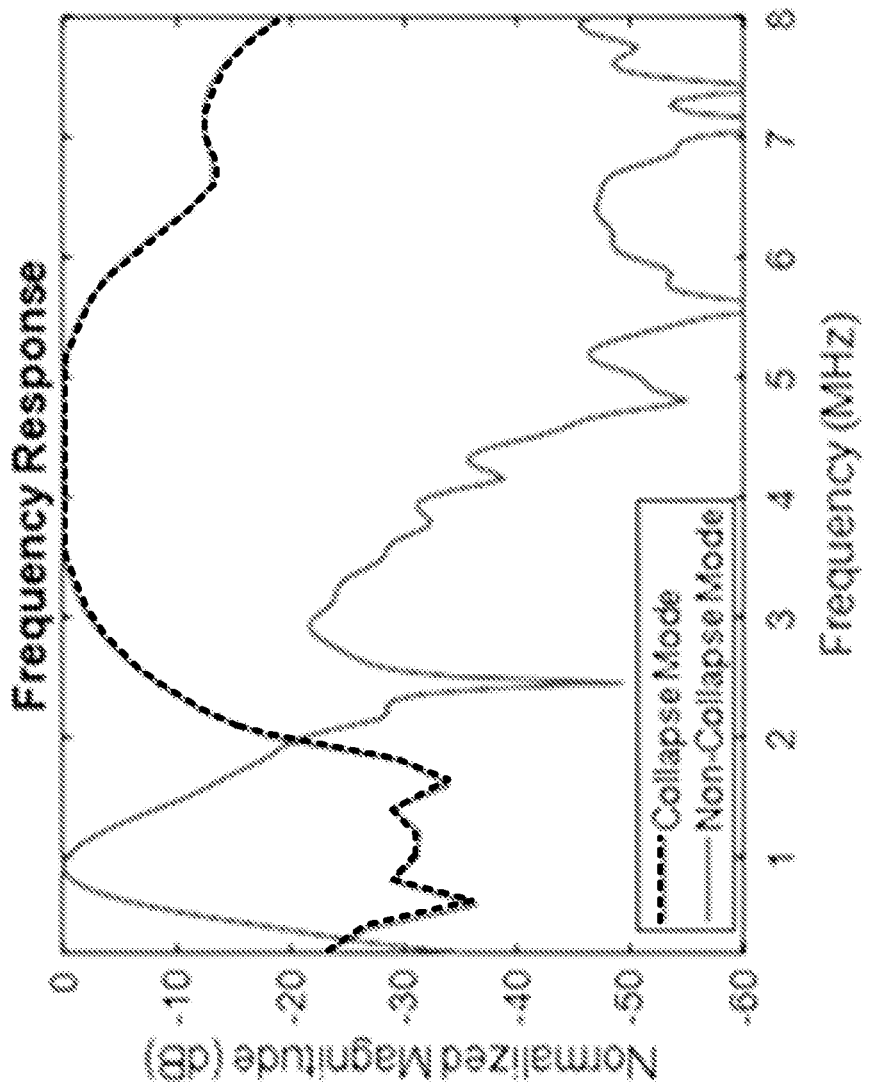
FIG. 3A shows measured receive sensitivity of a CMUT element biased at 50 volts (solid curve) in a non-collapsed mode, and a pulse-echo spectrum (dashed curve) of the CMUT element biased at 120 volts in a collapsed mode.

FIG. 3A shows measured receive sensitivity of a CMUT element biased at 50 volts (solid curve) in a non-collapsed mode, and a pulse-echo spectrum (dashed curve) of the CMUT element biased at 120 volts in a collapsed mode.

Figure 3B:
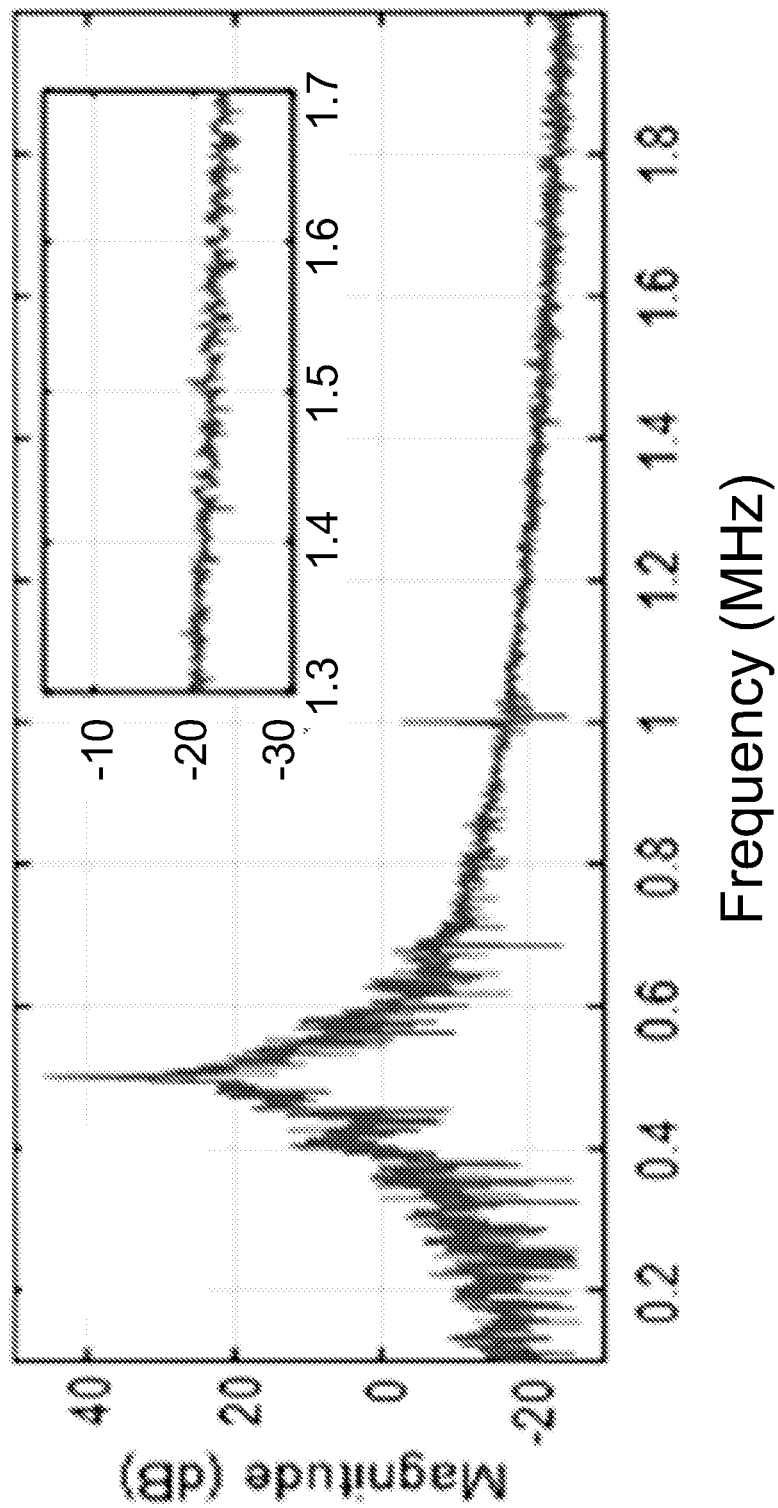
FIG. 3B shows a measured spectrum of a CMUT received signal (through a skull with water and a microbubble-filed tube) biased at 50 volts (non-collapsed mode).

FIG. 3B shows a measured spectrum of a CMUT received signal (through a skull with water and a microbubble-filed tube) biased at 50 volts (non-collapsed mode).

Figure 3C:
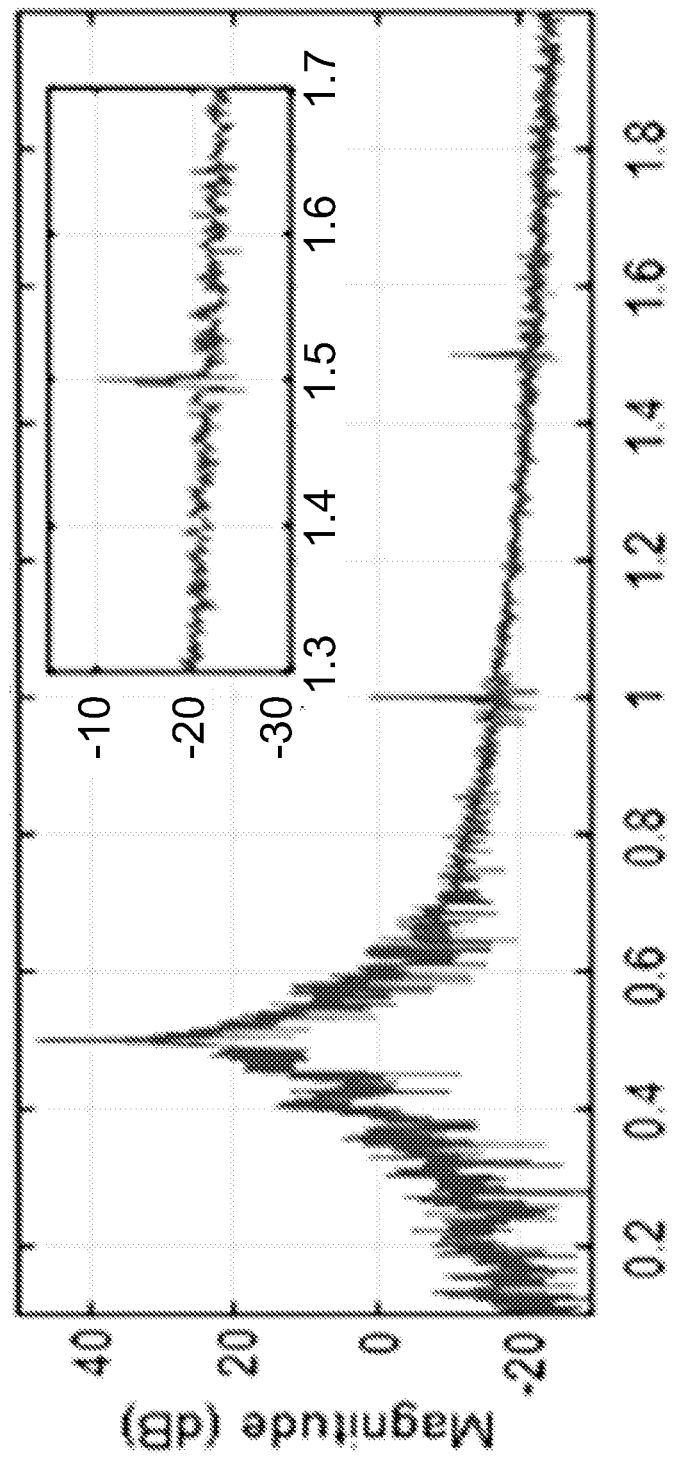
FIG. 3C shows a measured spectrum of a CMUT received signal (through a skull with water and microbubble-filed tube) biased at 120 volts (non-collapsed mode). The inset graph shows the enhanced microbubble harmonic detection in the collapsed mode.

FIG. 3C shows a measured spectrum of a CMUT received signal (through a skull with water and microbubble-filed tube) biased at 120 volts (collapsed mode). The inset graph shows the enhanced microbubble harmonic detection in the collapsed mode. High SNR detection of such weak acoustic emissions from microbubble oscillations in the 0.5-2 MHz may be utilized for expanding the safety margin of FUS, particularly for blood-brain-barrier disruption therapies (as shown in FIG. 2A). In certain implementations, the same CMUT sub-arrays used for active imaging (for co-registering with CT and MRI images) can be used as a single large and low noise receiver for this purpose based on methods like PAI.

Figure 4:
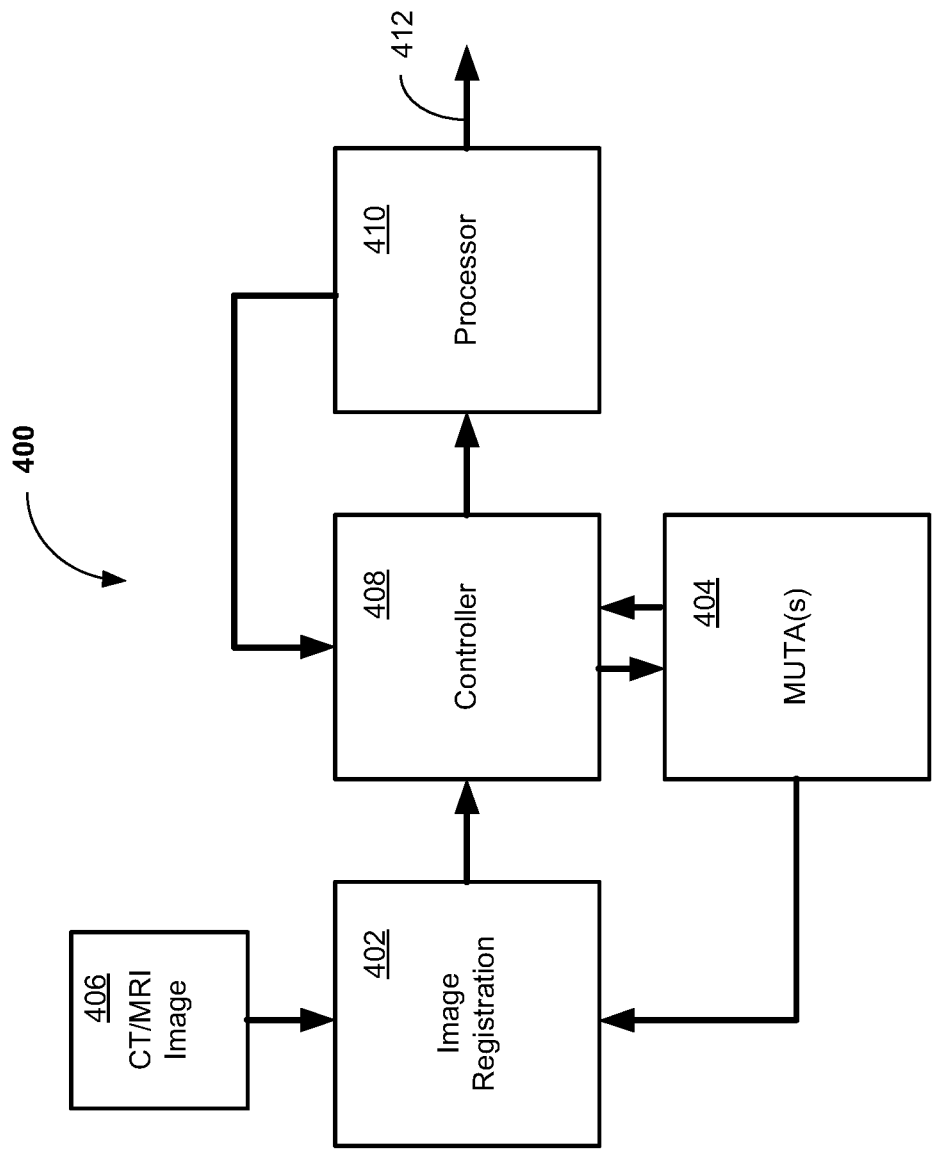
FIG. 4 is an example system diagram 400, according to an exemplary embodiment of the disclosed technology.

FIG. 4 is an example system diagram 400, according to an exemplary embodiment of the disclosed technology. In this example implementation, an image registration module 402 may be configured to receive signals 404 from one or more MUTAs and independently measured or derived images 406 (for example, from a previously obtained CT scan or MRI image, or simultaneously measured MRI image). In certain exemplary implementations, the image registration module may shift, rotate, and or scale one or more of the MUTA signals or the independently measured or derived images 406 to co-register the images for accurate FUS. In certain exemplary implementations, a controller 408 may be utilized in conjunction with one or more processors 410 to process the associated images/signals. In certain implementations, the processor 410 may provide an output 412, such as an image, image sequence, rendering, etc., to further aid the treatment.

Certain implementations of the disclosed technology may be utilized to capture features of a treatment region (for example, a skull surface and associate curvature) with high lateral and axial resolution. Certain implementations may use such information to accurately co-register the ultrasound images/signals with the MRI and/or pre-op CT images. For example, as discussed with reference to FIG. 1A, miniature, steerable, broadband imaging subarrays may be sparsely distributed on a secondary 3D shell (such as a helmet structure) and overlaid with a FUS system to overcome certain resolution and registration challenges and limitations that may be experienced using single (or few) elements. In one exemplary implementation, a 64 CMUT element 1D array with ±450 field of view and transmit beamforming electronics may be integrated on a 3 mm×10 mm silicon chip, as shown in FIG. 1B. One technical advantage of using such an array is that it can be operated with only a few cable connections. Certain exemplary implementations of the disclosed technology may utilize interlaced row-column addressed MUTAs (CMUT arrays and/or PMUT arrays) to reduce the number of interconnects.

Certain MUTAs disclosed herein may utilize geometrical designs to achieve the desired bandwidth. For example, element pitch (center-to-center separation) may be set to be approximately $\lambda/2$ where $\lambda$ is a wavelength of the desired detection frequency. As shown in FIG. 1C, a CMUT linear subarray having an element area of 78 μm$^2$ and 200 nm gap pitch may provide an imaging bandwidth of 2.5 to 4.3 MHz. In certain implementations, multiple linear subarrays may be configured for 3D imaging, in addition to multiple large angular span 2D cross-sections (as shown in FIG. 1B). As shown and described above with respect to FIG. 1A, and in certain exemplary implementations of the disclosed technology, subarrays can be fixed on a 3D printed shell that will fit into the FUS array with ~10° angular separation allowing overlapping Transmit/Receive (Tx/Rx) fields from multiple subarrays to be used to reconstruct a high-resolution image of the skull surface within few seconds.

In certain exemplary implementations, CMUT arrays can be fabricated on a separate silicon substrate using low-temperature fabrication processes. The electronics can be designed and fabricated using standard, low-cost CMOS processes (for example TSMC 0.18 µm, 70V BCD process). In certain exemplary implementations, CMUT array and electronics chips can be combined on a PCB with wire bonding with 5 micro-coax cables in total (3 DC bias, 1 data, and clock, 1 Rx signal) connected to each PCB to control and readout each subarray. The chips can be programmed using an FPGA synchronized with an ultrasound system.

According to an exemplary implementation of the disclosed technology, data may be collected from many sub-arrays (for example up to 1024 subarrays). In one exemplary implementation of the disclosed technology, such data may be collected using a Verasonics system. In certain exemplary implementations, locations of the subarrays on a support shell may be optimized to provide maximum coverage. For example, in the transcranial imaging application as depicted in FIG. 1A, a 3D shell having about 15 cm radius may be utilized and calibrated using an array of point targets placed over a human skull or phantom.

A suitable performance metric for this imaging sub-array system may be to obtain less than 1 mm in axial resolution and +400 field of view at 5 cm distance. In certain exemplary implementations of the disclosed technology, CMUT sub-arrays may be used to retrofit an existing piezoelectric FUS unit, for example, by placing the CMUTs in empty regions around the piezoelectric elements of the FUS unit. Simulations indicate that a 6.4 mm×6.4 mm sub-array size would allow obtaining 1 mm co-registration accuracy with MRI and CT images.

As shown in FIG. 1D and FIG. 1E, field II simulations (of the 2D imaging performance of 3 subarrays with 10° separation over a 3D shell with 15 cm radius of curvature) indicate that with this sparsity the subarrays (~16 subarrays over the 180° arc with 8 slices over the periphery) should cover a sufficient part of the skull surface to allow good image registration with high resolution within the acceptance angle of the array elements.

Certain exemplary implementations of the disclosed technology provide additional control variables to optimize certain performance results. One such control variable for improving SNR, as discussed above, includes setting the geometry of the elements and/or selectively connecting/disconnecting elements to adjust an effective detection area. Another control variable that may be used to increase output pressure is to utilize transmit beamforming. Yet another control variable that may be utilized to adjust a field of view includes changing element widths and/or selectively connecting/disconnecting elements to adjust an effective element width.

In accordance with certain exemplary implementations of the disclosed technology, some or all the elements of each CMUT subarray may be connected using on-chip switches to maximize the effective transducer area and enable high SNR. In certain implementations, the high SNR may be simultaneously enabled in each of the CMUT subarrays using such switching. Further implementations may utilize closely integrated low noise amplifiers to further improve the SNR performance close to the theoretical detection limits. To achieve a high coupling coefficient and low noise, CMUTs can be biased to 90% of their collapse voltage, which is approximately 18V for the designs shown in FIGS. 1A a 1B. Alternatively, the CMUTs can be used in the collapsed mode.

Simulations indicate that a detectable pressure level as low as 0.03 Pa with reasonable SNR may be sufficient to detect the acoustic emissions from a single oscillating microbubble (stable oscillations) after 15 cm of propagation (i.e. middle of the brain) and through an intact skull. In one exemplary implementation of the disclosed technology, an array with 128 CMUT elements, where each element has 78 µm square area membranes, can achieve a noise level close to the theoretical limit in 0.5 to 2 MHz bandwidth and about 0.0025 Pa detectable pressure when signals from the 128 elements (each with 6.4 mm×6.4 mm area) are averaged, as shown in FIG. 1F. Achieving this performance can provide −20 dB SNR for a single microbubble, which may expand the safety margin of the FUS blood-brain-barrier procedure to the theoretical limits. This type of sensitivity can also be used with other FUS applications in the body where the location of the microbubble activity or other mechanical/thermal processes generate signals in this broad frequency range.

In certain exemplary implementations, the CMUT membrane dimensions can vary from 20 µm up to 400 µm depending on the required center frequency. For example, for commercial CMUT arrays by Philips Innovations, the low-frequency variant (CM5-1) has a drum diameter of 350 µm, and for the high-frequency variant (CM12-5) has a drum diameter of 120 µm. The vacuum gap height and membrane thickness are the main parameters in the layer stack to be tuned. In applications where the CMUT is used as a transmitter, the CMUTs can be used in non-collapsed or collapsed mode. For example, if a commercial CMUT such as Philips Innovations CM5-1 transducer is used, the membranes can be circular with a diameter of 350 µm. These CMUTs have about 50V collapse voltage. When operated below this collapse voltage, these CMUTs can be used as transmitters for FUS-based treatment in the 300-500 kHz range. The same CMUTs can be biased above the collapse, such as 120V, and then they can be used for microbubble monitoring in the 1.5 MHz to 4.5 MHz range. For a typical CMUT array element in this frequency range, 33 of these membranes can be connected. The CMUT array elements can be 1D with a linear array configuration, 2D with row-column, or fully sampled configuration.

With the high-frequency CM12-5 arrays, with 120 µm diameter membranes, the operation frequency can be in the 1.5-2 MHz for non-collapsed mode operation and 4 MHz to 7 MHz range for collapsed and deep collapsed mode operation. In this high-frequency range, these arrays can be used to image the body section such as the skull surface with high resolution. The overall size of each of these arrays can be 1 mm×1 mm to 12 mm×12 mm, and in some cases like the 64-element CM5-1 array, it can be 12 mm×21 mm in size.

In accordance with certain exemplary implementations of the disclosed technology, the same subarray can be used for both active imaging and PAI by using the whole subarray area as a single receiver to reduce the noise and improve SNR by spatial averaging. In certain exemplary implementations, separate subarrays may be used for active imaging, and a single large CMUT element may be used for PAL. In certain exemplary implementations, each element can be larger than 40 $mm^2$ by taking advantage of the large area that may be available between the low-frequency piezoelectric FUS transmitters. In certain exemplary implementations, increasing the area of the array, subarray, and/or CMUT element may be used to increase sensitivity and SNR.

Certain exemplary implementations of the disclosed technology may include adaptive CMUT arrays for transcranial (or other) monitoring and mapping of microbubble dynamics. In such embodiments, individual CMUT receiver elements may be integrated with electronics, where some (or all) of the receiver elements can be configured as small, programmable receiver subarrays with the adaptive area and steerable directivity configured to control the receive sensitivity and noise. Thus, one of the technical improvements provided by the disclosed technology is that signals coming from a certain region of interest during FUS exposure may be optimized by the subarrays since they can be programmable in both size and directivity. In accordance with certain exemplary implementations of the disclosed technology, such low noise broadband CMUT receivers may be integrated into an MRgFUS system made of piezo-ceramic transducers to provide a versatile platform with high power output and low-noise, high-sensitivity receive operation over the bandwidth of interest.

Certain aspects of the disclosed technology may improve FUS therapy via enhanced microbubble dynamics monitoring. Certain implementations may be utilized to increase the detection sensitivity for monitoring microbubble acoustic emissions. Certain implementations of the disclosed technology may enhance the ability to characterize and monitor nonlinear microbubble dynamics. Certain implementations may integrate CMUTs with low noise integrated electronics to enable detection of acoustic signals close to the theoretical radiation impedance limited levels. Certain implementations of the disclosed technology can utilize low noise receivers for FUS monitoring by constructing a sparse array of receivers over a 3D printed shell that will fit into a clinical scale Magnetic Resonance guided FUS (MRgFUS) system (as depicted in FIG. 1A). The disclosed technology may further utilize methods to determine optimum exposure settings for an application of FUS-mediated brain-blood-barrier opening. Certain implementations may improve the effectiveness of FUS by reducing the measurement uncertainty in the onset, location, and type (stable vs inertial) of cavitation activity during the FUS exposures. The systems and methods disclosed herein may be applied to other FUS applications, including histotripsy thermal ablation, and drug delivery, in other parts of the body.

To be able to detect the microbubble emissions with high sensitivity, certain implementations of the disclosed technology may optimize the SNR of the receiver using adaptive CMUT sub-arrays. As discussed above with respect to FIG. 1A, in which a 2×2 subarray is depicted, the SNR may be improved using 3×3, 4×4, or larger subarrays such as 10×10. In addition to low noise operation, one advantageous characteristic of the 2D CMUT subarray is that its field of view (i.e. directivity) can be adjusted to optimize the receive sensitivity. In accordance with certain exemplary implementations of the disclosed technology, element directivity may be controlled via integrated electronics that include switch and delay circuits connected to individual CMUT elements or sub-groups of CMUTs. In certain exemplary implementations, such switch and/or delay circuits may be utilized to adjust the effective area of the CMUT receiver. In certain exemplary implementations, such switch and/or delay circuits may be utilized to steer the sub-array, for example, to preset angles that can help the overall sparse array to effectively scan the brain. In accordance with certain exemplary implementations of the disclosed technology, the delay circuits can be analog programmable delay circuits. In other example implementations, the delay circuits can be digital programmable delay circuits.

In accordance with certain exemplary implementations of the disclosed technology, the sub-array may be fabricated on a silicon substrate. An advantage of such fabrication is that electronics may be integrated with the CMUT technology using a standard, low-cost IC process, such as that available from MOSIS. In certain exemplary implementations, the CMUT sub-array and electronics chips may be combined on a PCB by wire-bonding. As discussed above with reference to FIG. 2B, a total of 5 micro-coaxials cables (3 for DC bias and ground, 1 data and clock, 1 Rx signal) may be routed to each PCB to control and readout signals from each sub-array. To achieve a high coupling coefficient and low noise, CMUTs can be biased to 80-90% of their collapse voltage (18 V at 80% bias, for example), or they can be used in collapsed mode. In other exemplary implementations, arrays may be fabricated monolithically using the CMUT-on-CMOS.

Certain exemplary implementations of the disclosed technology may leverage the complementary strengths of the piezoelectric and CMUT technologies by integrating a CMUT array made of up to 128 to up to 1024 or more sub-array elements with a clinical scale (15 cm radius of curvature) piezo ceramic sparse FUS phased array. Accordingly, the locations of the adaptive CMUT sub-array elements and 256 element FUS piezoelectric arrays may be integrated (i.e. the CMUT sub-arrays may be disposed on top of the FUS array on a shell) and calibrated using acoustic triangulation. In certain exemplary implementations, a PAI-based FUS control system can be connected to the adaptive CMUT receiver array as shown in FIG. 2B (where only a single CMUT sub-array is depicted). In accordance with certain exemplary implementations of the disclosed technology, an FPGA-based system can be synchronized with the PAI computer to generate the clock and control the data flow to the CMUT elements. The operation parameters of the integrated adaptive system can be optimized by evaluating the SNR of the PAI using a calibrated point source (hydrophone). In certain exemplary implementations, the parameters to optimize may include the number and location of active CMUT array elements (aperture on the 3D shell) and their steering angles to effectively scan for microbubble activity inside and outside the skull.

Considering that CMUTs can provide nearly 10× better noise performance with larger bandwidth (0.5 Pa over >4 MHz bandwidth) as compared to piezo composite receivers (3.42 Pa over >4 MHz bandwidth), using CMUTs for microbubble detection through the skull is well justified. As discussed above, a 128 element CMUT array (each with 6.4 mm×6.4 mm area) may theoretically achieve a noise level close to about 0.025 Pa in 0.5-2 MHz bandwidth when signals from the 128 elements are averaged. Achieving this performance would provide −20 dB SNR for a single microbubble detection. The feature may further enable imaging stable microbubble oscillations and tracking their kinetics in the brain towards optimizing the microbubble administration protocols and controller operation.

TABLE 1

Example specifications of a sparse CMUT array.

| Receiver | Source | Excitation/ Receive Freq. | Geometry (receiver vs source) | Microbubble Dose |
|---|---|---|---|---|
| Sparse CMUT array on 3D shell | FUS excited bubble | 0.2-0.4 MHz/ 0.4-2 MHz | Angles: 0-60° Distance: 1-10 cm bubble-activity: 1-5 cm | 0.1-1000 bubbles/μl |

Although the example specifications depicted in Table 1 may be suitable for therapy guidance for brain-blood-barrier opening type of applications, with detection frequencies in the 0.2 MHz to 2 MHz range, certain CMUT sub-arrays may be utilized for a wider frequency range from 0.1 MHz to above 20 MHz by using very thin membranes or membranes with multiple lateral sizes to cover different frequency ranges. In certain exemplary implementations, multifunctional skull imaging/broadband receiving CMUT arrays may be combined with an adaptive receiver to provide additional capabilities.

In certain exemplary implementations, some of the functions and/or capabilities of the MUTAs can be achieved using piezoelectric micromachined ultrasonic transducer (PMUT) technology as discussed in Jiang, Xiaoyue, Hao-Yen Tang, Yipeng Lu, Eldwin J. Ng, Julius M. Tsai, Bernhard E. Boser, and David A. Horsley. "Ultrasonic fingerprint sensor with transmit beamforming based on a PMUT array bonded to CMOS circuitry." IEEE transactions on ultrasonics, ferroelectrics, and frequency control 64, no. 9 (2017): 1401-1408, which is incorporated herein by reference as if presented in full. PMUTs, for example, can be integrated with electronics and can be used to generate beamformed focused ultrasound beams for treatment. PMUTS may also be used as receivers, albeit with less bandwidth than CMUTs. As with CMUTs, the frequency response of the treatment and monitoring arrays using PMUTS may be adjusted by changing the membrane lateral geometry from 5-1000 micrometers and/or by changing the thickness of the PMUT membranes from 100 nm to 15 um.

In this disclosure, several descriptions have been presented to provide an understanding of CMUT frequency response and sensitivity in transmit and receiver mode. Certain implementations may rely on the DC bias applied between the top and bottom electrodes of the CMUT. In the transmit mode, for example, a CMUTs can be used without a DC bias and the output frequency of the generated pressure may be twice the input frequency. Such a no DC bias case may be utilized to maximize the output pressure for treatment. With DC bias applied to the CMUT, the device can be used as a receiver and may be a more efficient transmitter. At low bias voltages, this operation mode is called the conventional or non-collapsed mode. This mode can be used for broadband reception and high amplitude transmission at a lower frequency (100 kHz-1 MHz). When the DC bias is increased to a point that the electrostatic forces overcome the restoring force of the membrane, the CMUT membrane collapses. In this case, the resonance frequency of the device moves to a higher frequency as the center of the membrane is now in contact with the substrate. This is called the collapsed mode. By increasing the bias, the contact area increases, and the frequency shifts to even higher frequencies. In this case, where a significant portion of the membrane is in contact with the substrate during the transmit cycle is called the deep-collapse mode. Further information regarding the collapsed and non-collapsed modes may be found in Oralkan, Omer, Baris Bayram, Goksen G. Yaralioglu, A. Sanli Ergun, Mario Kupnik, David T. Yeh, Ira O. Wygant, and Butrus T. Khuri-Yakub. "Experimental characterization of collapse-mode CMUT operation." IEEE transactions on ultrasonics, ferroelectrics, and frequency control 53, no. 8 (2006): 1513-1523, which is incorporated herein by reference as if presented in full. Further information regarding the deep-collapse mode may be found in Olcum, Selim, F. Yalcin Yamaner, Ayhan Bozkurt, and Abdullah Atalar. "Deep-collapse operation of capacitive micromachined ultrasonic transducers." IEEE transactions on ultrasonics, ferroelectrics, and frequency control 58, no. 11 (2011): 2475-2483, which is incorporated herein by reference as if presented in full.

In certain exemplary implementations, the DC bias dependent control of the CMUT can allow one to use part of the CMUT for low frequency (100 kHz to 1 MHz) transmit for treatment in non-collapsed mode, and the other part in a collapsed mode for detection and monitoring at harmonic frequencies (200 kHz to 4 MHz) by applying a DC voltage larger than the collapse voltage. Similarly, to image the skull or other body parts with high resolution, the same CMUT can be used in collapsed or deep-collapsed mode to achieve even higher frequencies (4 MHz to 10 MHz). Similar effects can be obtained by a single CMUT array but using separate regions with different membrane geometries.

Figure 5:
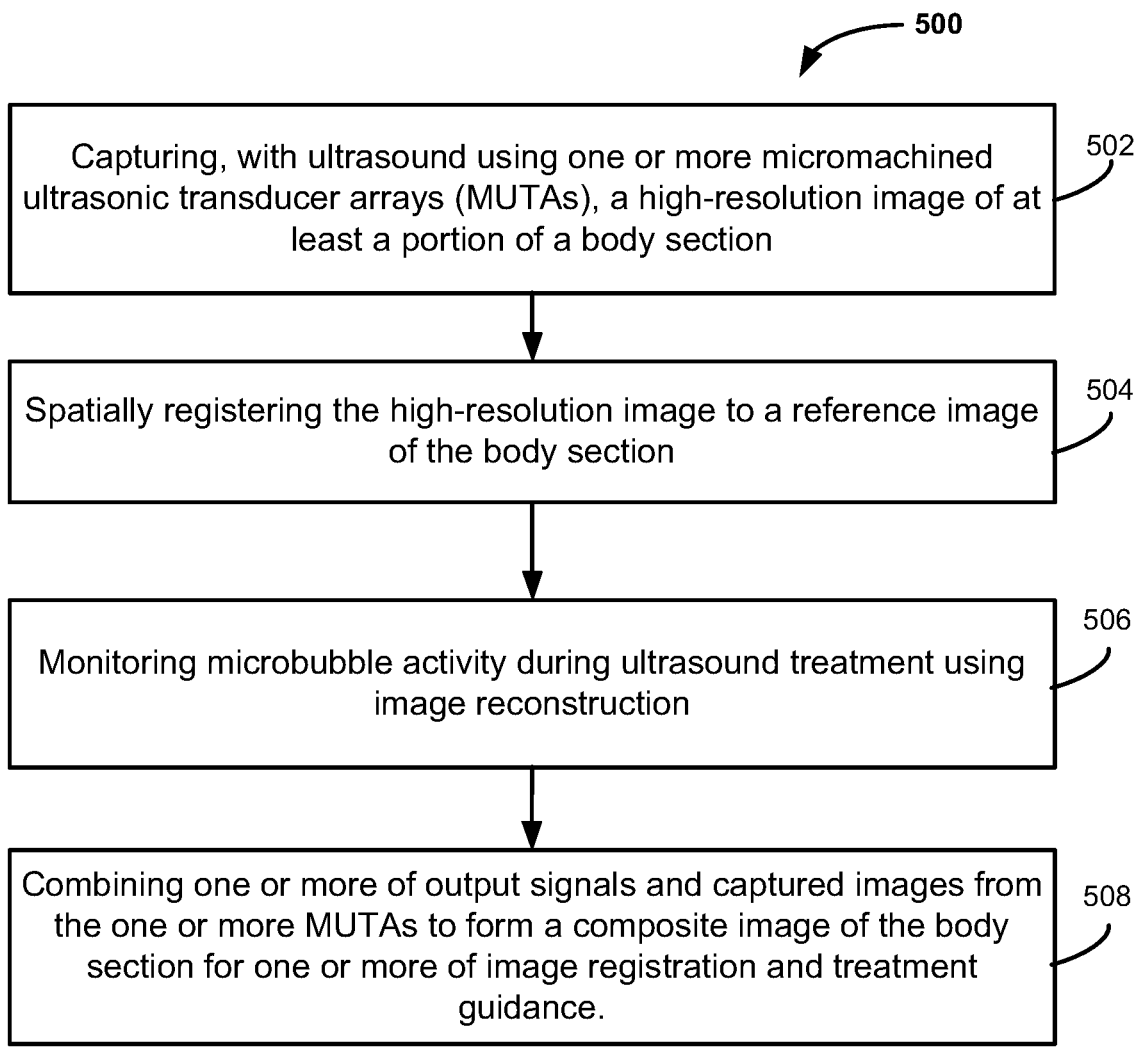
FIG. 5 is a flow diagram of a method 500, according to an exemplary implementation of the disclosed technology.

FIG. 5 is a flow diagram of a method 500, according to an exemplary implementation of the disclosed technology. In block 502, method 500 includes capturing, with ultrasound using one or more micromachined ultrasonic transducer arrays (MUTAs), a high-resolution image of at least a portion of a body section. In block 504, method 500 includes spatially registering the high-resolution image to a reference image of the body section. In block 506, method 500 includes monitoring microbubble activity during ultrasound treatment using image reconstruction. In block 508, method 500 includes combining one or more of output signals and captured images from the one or more MUTAs to form a composite image of the body section for one or more of image registration and treatment guidance.

Figure 6:
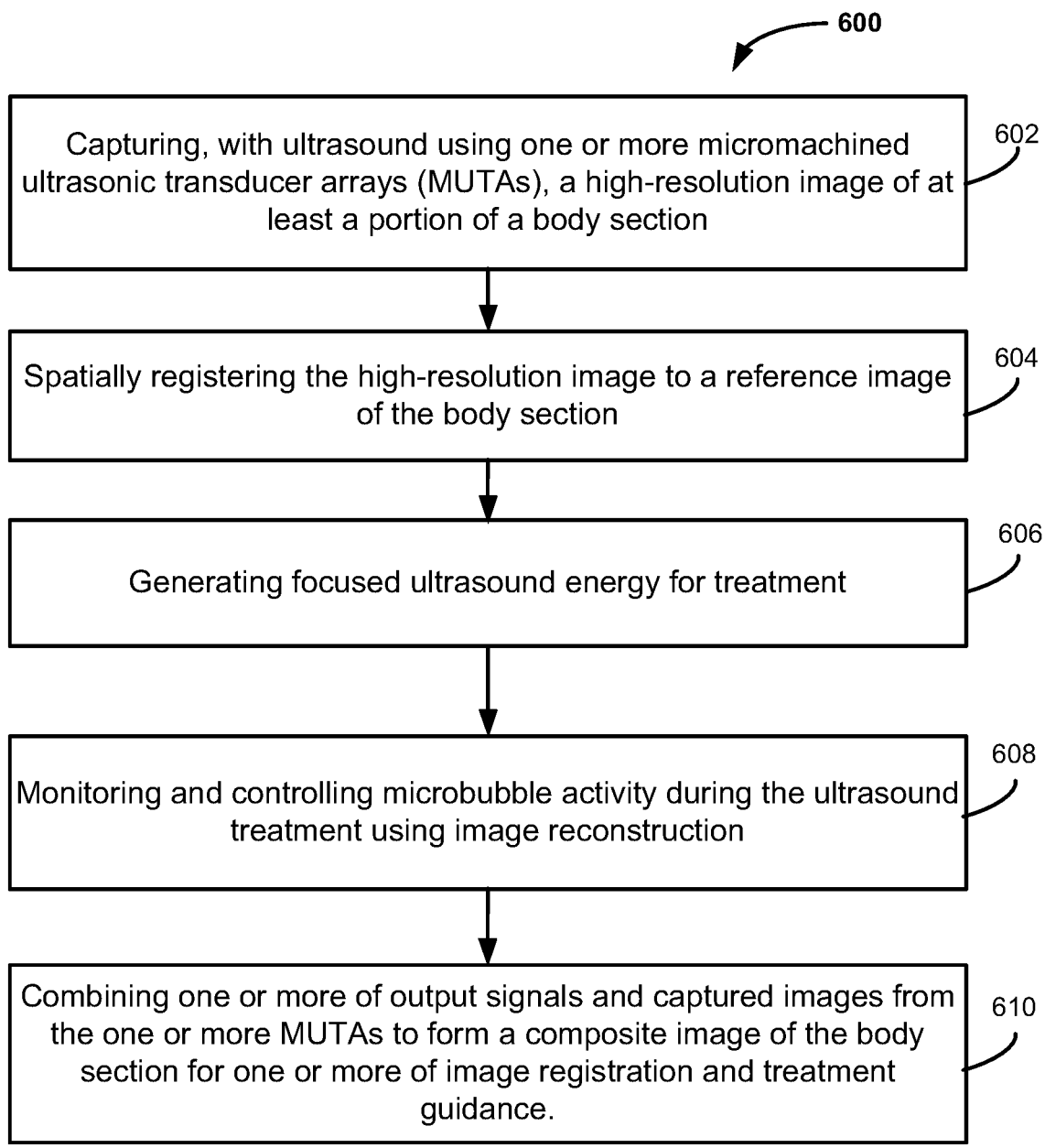
FIG. 6 is a flow diagram of a method 600, according to an exemplary implementation of the disclosed technology.
Figure 7A:
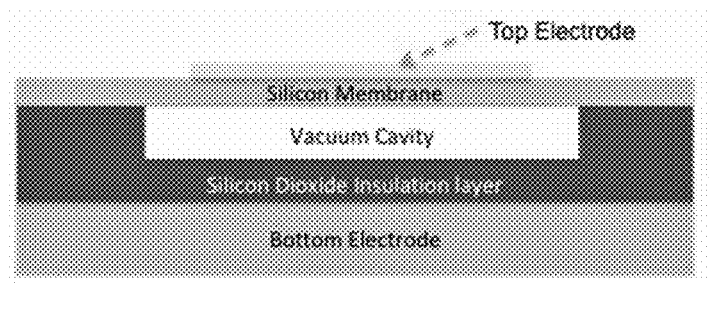
FIGS. 7A-7C illustrate a CMUT structure (FIG. 7A) and two modes of operation (FIGS. 7B-7C) of the CMUT, according to an exemplary implementation of the disclosed technology.
Figure 7B:
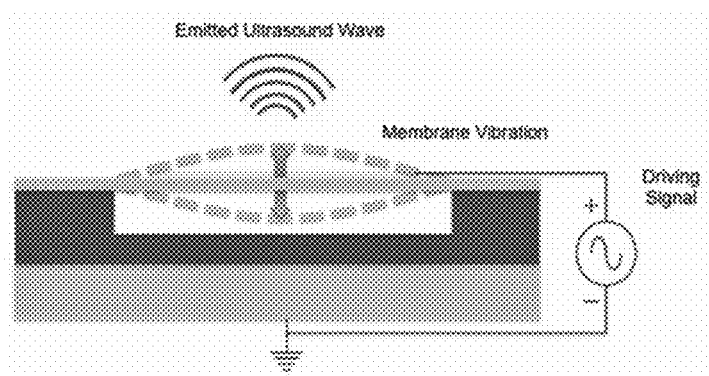
Figure 7C:
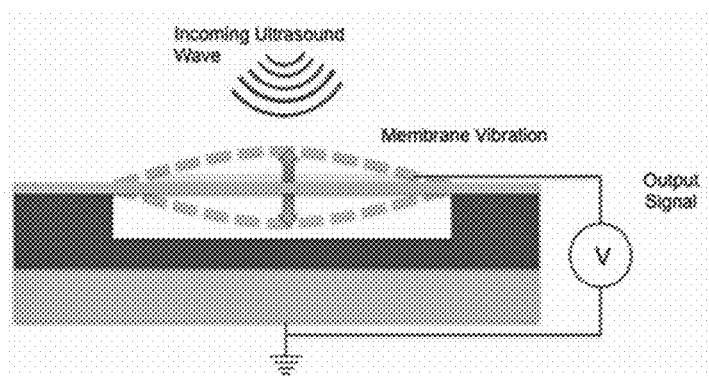

FIG. 6 is a flow diagram of a method 600, according to an exemplary implementation of the disclosed technology. In block 602, method 600 includes capturing, with ultrasound using one or more micromachined ultrasonic transducer arrays (MUTAs), a high-resolution image of at least a portion of a body section. In block 604, method 600 includes spatially registering the high-resolution image to a reference image of the body section. In block 606, method 600 includes generating focused ultrasound energy for treatment. In block 608, method 600 includes monitoring and controlling microbubble activity during ultrasound treatment using image reconstruction. In block 612, method 600 includes combining one or more of output signals and captured images from the one or more MUTAs to form a composite image of the body section for one or more of image registration and treatment guidance.

Certain exemplary implementations of the disclosed technology may include electrically connecting two or more elements of the MUTAs by switching, an on-chip switch to adapt an effective transducer area of the one or more MUTAs for improving a signal-to-noise ratio.

Certain exemplary implementations of the disclosed technology may include coupling at least one of the one or more MUTAs with electronics. Certain exemplary implementations of the disclosed technology can include controlling one or more of drive signal amplitude, frequency filtering, multiplexing, and DC biasing with the electronics.

The disclosed technology includes a multifunctional ultrasound system for performing any of the methods disclosed herein, including but not limited to body section registration, mapping of microbubble dynamics, and ultrasound treatment. The system can include one or more micromachined ultrasonic transducer arrays (MUTAs) configured to capture a high-resolution image of at least a portion of a body section using ultrasound, monitor and control microbubble activity during ultrasound treatment, and generate focused ultrasound energy for treatment. Certain implementations of the system can include an image registration module configured to spatially register the high-resolution image with a reference image. Certain implementations of the system can include electronics configured to control one or more of drive signal amplitude, frequency filtering, multiplexing and/or DC biasing. In certain exemplary implementations, the electronics may be configured to control a DC bias voltage to adapt a frequency response of at least one CMUT of the one or more MUTAa by causing the at least one CMUT to operate in one or more of a non-collapsed mode, a collapsed mode, and a deep-collapsed mode.

In certain implementations, the system can include one or more on-chip switch(es) in communication with at least two elements of the MUTAs. The on-chip switch(es) can be configured to adapt an effective transducer area of the one or more MUTAs for improving an effective SNR of the system.

In accordance with certain exemplary implementations, the systems and/or methods disclosed herein may be characterized by one or more of the following:

- Electronics may be integrated with at least one of the one or more MUTAs.
- Electronics may be configured to control a DC bias voltage to adapt a frequency response of at least one of the MUTAs.
- At least one of the one or more MUTAs can be a capacitive micromachined ultrasonic transducer (CMUT).
- The electronics may be configured to control a DC bias voltage to cause the one or more CMUTs to operate in one or more of a non-collapsed mode, a collapsed mode, and a deep-collapsed mode.
- The body section can include one or more of a skull, a skull-brain interface, a brain, a liver, and an organ.
- The one or more MUTAs can include one or more capacitive micromachined ultrasonic transducers (CMUTs).
- The one or more MUTAs can include one or more piezoelectric micromachined ultrasonic transducers (PMUTs).
- The DC bias voltage may be configured or adjusted to cause the one or more MUTAs to operate in one or more of a non-collapsed mode, a collapsed mode, and a deep-collapsed mode.
- The reference image can include one or more of a CAT scan image, a PET scan image, and an MRI image.
- The one or more MUTAs may be adapted by one or more of frequency response, output power, and spatial distribution over each array surface.
- Two or more MUTAs may be disposed on a common substrate to adapt target frequency responses for one or more of ultrasound imaging of the body section for image registration, ultrasound monitoring of microbubble activity, and generating ultrasound for treatment.
- A target frequency response for capturing the image of the body section for image registration may be in a range of 2 MHz to 15 MHz.
- A target frequency response for ultrasound monitoring of microbubble activity may be in a range of 50 kHz to 5 MHz.
- A target frequency response for generating ultrasound for treatment may be in a range of 50 kHz to 1 MHz.
- The target frequency response for ultrasound monitoring of microbubble activity may be adapted to be complementary to at least a portion of the target frequency response and/or drive frequency for generating the ultrasound for treatment by using one or more of electronic filtering and DC biasing. In this respect, interference in the received monitoring signal due to the ultrasound generation drive signal may be reduced, minimized, and/or eliminated
- Two or more MUTAs can be characterized by different membrane geometries.
- The membrane geometries may be characterized by lateral dimensions between 5 μm and 250 μm.
- The membrane geometries may be characterized by lateral dimensions between 250 μm and 1000 μm.
- The one or more MUTAs may be configured to detect activity of 1 to 5 microbubbles during ultrasound treatment.
- The one or more MUTAs may be configured to detect activity of 5 to 10 microbubbles during ultrasound treatment.
- The one or more MUTAs may be configured to detect activity of 10 to 20 microbubbles during ultrasound treatment.
- The one or more MUTAs may be configured to detect activity of 20 to 100 microbubbles during ultrasound treatment.
- The one or more MUTAs may be configured to detect activity of 100 to 1000 microbubbles during ultrasound treatment.
- The one or more MUTAs may be configured to detect activity of 1000 to 10,000 microbubbles during ultrasound treatment.
- The one or more MUTAs may be configured to detect activity of 1 to 1000 microbubbles during ultrasound treatment.
- The monitoring and/or controlling microbubble activity during the ultrasound treatment can include monitoring activity of 1 to 1000 microbubbles during the ultrasound treatment.
- The one or more MUTAs may capture and/or may be configured to capture the high-resolution image and monitor microbubble activity at a diffraction-limited spatial resolution.
- The one or more MUTAs may be individually adaptable to monitor microbubble activity in a body section.
- At least one of the one or more MUTAs may be configured to individually generate an image of a portion of the body section.
- At least one of the one or more MUTAs may be configured to monitor microbubble activity in a specific body section.
- At least one of the one or more MUTAs may be configured to image a specific region of the body section for image registration.
- At least one of the one or more MUTAs may be configured to image a specific region of the body section for treatment guidance.
- The image reconstruction can include plane wave spectrum combinations, delay and sum, phased array, synthetic aperture, and/or short spatial coherence.
- Certain implementations may be configured to maintain stable cavitation during treatment using a control loop and an output signal of the one or more MUTAs.
- Certain implementation can include a control loop configured to maintain stable cavitation using an output signal of the one or more MUTAs.
- In certain implementations, the focused ultrasound energy for treatment may be generated using one or more piezoelectric micromachined ultrasonic transducer array (PUTAs).

In certain implementations, the focused ultrasound energy for treatment may be generated using one or more MUTAs.

Although preferred embodiments of the disclosed technology are explained in detail, it is to be understood that other embodiments are contemplated. Accordingly, it is not intended that the disclosed technology is limited in its scope to the details of construction and arrangement of components set forth in the following description or illustrated in the drawings. The disclosed technology is capable of other embodiments and of being practiced or carried out in various ways. As used in the specification and the appended claims, the singular forms "a," "an," and "the" include plural referents unless the context clearly dictates otherwise.

It is intended that each term presented herein contemplates its broadest meaning as understood by those skilled in the art and may include all technical equivalents, which operate in a similar manner to accomplish a similar purpose.

Ranges may be expressed herein as from "about" or "approximately" one particular value and/or to "about" or "approximately" another particular value. When such a range is expressed, another embodiment may include from the one particular value and/or to the other particular value. Similarly, values may be expressed herein as "about" or "approximately."

The terms "comprising" or "containing" or "including" means that at least the named element, material, or method step is present in the apparatus or method, but does not exclude the presence of other elements, materials, and/or method steps, even if the other elements, materials, and/or method steps have the same function as what is named.

The term "exemplary" as used herein is intended to mean "example" rather than "best" or "optimum."

Numerous characteristics and advantages have been set forth in the foregoing description, together with details of structure and function. While the disclosed technology has been presented in several forms herein, it may be apparent to those skilled in the art that many modifications, additions, and deletions, especially in matters of shape, size, and arrangement of parts, can be made therein without departing from the spirit and scope of the disclosure and its equivalents as set forth in the following claims. Therefore, other modifications or embodiments as may be suggested by the teachings herein are particularly reserved as they fall within the breadth and scope of the claims.

We claim:

1. A system comprising:
   a first micromachined ultrasonic transducer array (MUTA) comprising one or more capacitive micromachined ultrasonic transducers (CMUTs) having a collapse voltage and comprising a substrate, a substrate electrode, edges, a suspended membrane constrained at the edges and suspended over the substrate, a membrane electrode, and a gap between the suspended membrane and the substrate; and
   electronics configured to control a vibrational mode of the CMUTs via application of a DC bias voltage across the electrodes of the CMUTs;
   wherein:
      the MUTA is configured to:
         capture a high-resolution image of at least a portion of a body section using ultrasound; and
         monitor microbubble activity during ultrasound treatment;
      the vibrational mode is selected from the group consisting of a non-collapsed mode, a collapsed mode, and a deep-collapsed mode;
      in the non-collapsed mode, the DC bias voltage is less than the collapse voltage, and vibration of the membrane between the constrained edges is free of contact with the substrate;
      in the collapsed mode, the DC bias voltage is the collapse voltage, and vibration of the membrane between the constrained edges is not free of contact with the substrate, with a first central portion of the membrane spanning across the gap and coming into contact with the substrate, thereby constraining the membrane at the edges and along a length of the first central portion; and
      in the deep-collapsed mode, the DC bias voltage is greater than the collapse voltage, and vibration of the membrane between the constrained edges is not free of contact with the substrate, with a second central portion of the membrane, being greater than the first central portion, spanning across the gap and coming into contact with the substrate, thereby constraining the membrane at the edges and along a length of the second central portion.

2. The system of claim 1 further comprising:
   an image registration module configured to spatially register the high-resolution image with a reference image;
   wherein the electronics is further configured to control one or more of drive signal amplitude, frequency filtering, and multiplexing; and
   wherein the electronics are integrated with the MUTA.

3. The system of claim 1, wherein the body section is selected from the group consisting of a skull, a skull-brain interface, a brain, a liver, an organ, and combinations thereof.

4. The system of claim 1 further comprising:
   a second MUTA; and
   an on-chip switch in communication with the MUTAs;
   wherein the on-chip switch is configured to adapt an effective transducer area of at least one of the MUTAs for improving an effective signal-to-noise ratio (SNR) of the system.

5. The system of claim 1, wherein the reference image is selected from the group consisting of a CAT scan image, a PET scan image, an MRI image, and combinations thereof.

6. The system of claim 4, wherein the MUTAs are adaptable by one or more of frequency response, output power, and spatial distribution over each array surface.

7. A multifunctional ultrasound system for body section registration and mapping of microbubble dynamics comprising:
   a first micromachined ultrasonic transducer array (MUTA) and one or more second MUTAs, the MUTAs comprising ultrasonic transducers having a membrane, wherein two or more of the ultrasonic transducers comprise different membrane geometries; and
   an image registration module configured to spatially register the high-resolution image with a reference image;
   wherein:
      (i) at least two of the MUTAs are disposed on a common substrate to adapt target frequency responses for at least one of:
         ultrasound imaging of the body section for image registration;
         ultrasound monitoring of microbubble activity; or
         generating ultrasound for treatment;
      (ii) at least one of:
         the target frequency response for ultrasound monitoring of microbubble activity is adapted to be complementary to at least a portion of the target frequency response for generating the ultrasound for treatment by using at least one of electronic filtering or DC biasing;

each MUTA is configured to at least one of:
monitor microbubble activity in a specific body section using image reconstruction;
control microbubble activity during ultrasound treatment using image reconstruction;
image a specific region of the body section for image registration; or
image a specific region of the body section for treatment guidance;
wherein the image reconstruction comprises at least one of plane wave spectrum combinations, delay and sum, phased array, synthetic aperture, or short spatial coherence; and (iii) at least one of:
a target frequency response for capturing the image of the body section for image registration is in a range of 2 MHz to 15 MHz;
a target frequency response for ultrasound monitoring of microbubble activity is in a range of 50 kHz to 5 MHz;
a target frequency response for generating ultrasound for treatment is in a range of 50 kHz to 1 MHz;
the different membrane geometries are characterized by lateral dimensions between 5 µm and 250 µm;
the different membrane geometries are characterized by lateral dimensions between 250 µm and 1000 µm;
the MUTAs are configured to detect activity of 1 to 1000 microbubbles during ultrasound treatment;
the MUTAs are configured to capture the high-resolution image and monitor microbubble activity at a diffraction-limited spatial resolution;
each MUTA is individually adaptable to monitor microbubble activity in a body section; or
each MUTA is configured to individually generate an image of a portion of the body section.

8. The system of claim 7, wherein the system is configured to spatially map at least one of the microbubble activity or image the body section by image reconstruction.

9. A multifunctional ultrasound system for body section registration and mapping of microbubble dynamics comprising:
a first micromachined ultrasonic transducer array (MUTA) and one or more second MUTAs, the MUTAs comprising ultrasonic transducers having a membrane;
an image registration module configured to spatially register the high-resolution image with a reference image; and
a control loop configured to maintain stable cavitation using an output signal of the MUTAs;
wherein at least two of the MUTAs are disposed on a common substrate to adapt target frequency responses for at least one of:
ultrasound imaging of the body section for image registration;
ultrasound monitoring of microbubble activity; or
generating ultrasound for treatment; and
wherein at least one of:
the target frequency response for ultrasound monitoring of microbubble activity is adapted to be complementary to at least a portion of the target frequency response for generating the ultrasound for treatment by using at least one of electronic filtering or DC biasing;

two or more of the ultrasonic transducers comprise different membrane geometries; or
each MUTA is configured to at least one of:
monitor microbubble activity in a specific body section using image reconstruction;
control microbubble activity during ultrasound treatment using image reconstruction;
image a specific region of the body section for image registration; or
image a specific region of the body section for treatment guidance;
wherein the image reconstruction comprises at least one of plane wave spectrum combinations, delay and sum, phased array, synthetic aperture, or short spatial coherence.

10. The system of claim 7, wherein the MUTAs are further configured to generate focused ultrasound energy for treatment.

11. The system of claim 7, wherein the MUTAs are further configured to control the microbubble activity during the ultrasound treatment.

12. A method for body section image registration, mapping of microbubble dynamics, and ultrasound treatment with the system of claim 7 comprising:
capturing, with ultrasound using the MUTAs, the high-resolution image;
spatially registering with the image registration module the high-resolution image to the reference image;
generating, with at least one of the MUTAs, focused ultrasound energy for ultrasound treatment;
monitoring and controlling, with at least one of the MUTAs, microbubble activity during the ultrasound treatment; and
combining one or more of output signals and captured high-resolution images from the MUTAs to form a composite image of the body section for at least one of image registration or treatment guidance.

13. The method of claim 12, wherein one or more of the MUTAs each comprise one or more capacitive micromachined ultrasonic transducers (CMUTs); and
wherein the method further comprises adjusting a DC bias voltage to cause at least one of the CMUTs to operate in at least one of a non-collapsed mode, a collapsed mode, or a deep-collapsed mode.

14. The method of claim 12 further comprising electrically connecting two or more elements of the MUTAs by an on-chip switch to adapt an effective transducer area of the MUTAs for improving a signal-to-noise ratio (SNR).

15. The method of claim 12 further comprising:
disposing two or more MUTAs on a common substrate to adapt target frequency responses for at least one of ultrasound imaging of the body section for image registration, ultrasound monitoring of microbubble activity, or generating ultrasound for treatment; and
adapting the target frequency response for ultrasound monitoring of microbubble activity to be complementary to at least a portion of the target frequency response for generating the ultrasound for treatment by using at least one of electronic filtering or DC biasing;
wherein a target frequency response for the ultrasound imaging of the body section for image registration is in a range of 2 MHz to 15 MHz;
wherein a target frequency response for ultrasound monitoring of microbubble activity is in a range of 50 kHz to 5 MHz; and
wherein a target frequency response for generating ultrasound for treatment is in a range of 50 kHz to 1 MHz.

16. A multifunctional ultrasound system for body section registration, mapping of microbubble dynamics, and ultrasound treatment, the system comprising:
one or more micromachined ultrasonic transducer arrays (MUTAs) comprising ultrasonic transducers, each MUTA configured to:
capture a high-resolution image of at least a portion of a body section using ultrasound;
monitor and control microbubble activity during ultrasound treatment; and
generate focused ultrasound energy for treatment;
an image registration module configured to spatially register the high-resolution image with a reference image; and
electronics configured to control a DC bias voltage to cause at least of the one ultrasonic transducers to operate in a different mode from another of the one or more ultrasonic transducers, the modes selected from a group consisting of a non-collapsed mode, a collapsed mode, and a deep-collapsed mode.

17. The system of claim 16, wherein the electronics are integrated with at least one of the one or more MUTAs; and
wherein the electronics are further configured to control at least one of drive signal amplitude, frequency filtering, or multiplexing.

18. The system of claim 16 further comprising at least one on-chip switch in communication with at least two elements of the MUTAs;
wherein the at least one on-chip switch is configured to adapt an effective transducer area of the one or more MUTAs for improving an effective SNR of the system.

19. The system of claim 16, wherein two or more MUTAs are disposed on a common substrate to adapt target frequency responses for at least one of ultrasound imaging of the body section for image registration, ultrasound monitoring of microbubble activity, or generating ultrasound for treatment;
wherein a target frequency response for capturing the image of the body section for image registration is in a range of 2 MHz to 15 MHz;
wherein a target frequency response for ultrasound monitoring of microbubble activity is in a range of 50 kHz to 5 MHz; and
wherein a target frequency response for generating ultrasound for treatment is in a range of 50 kHz to 1 MHz.

20. The system of claim 19, wherein the target frequency response for ultrasound monitoring of microbubble activity is adapted to be complementary to at least a portion of the target frequency response for generating the ultrasound for treatment by using at least one of electronic filtering or DC biasing.

21. The system of claim 19, wherein the two or more MUTAs comprise different membrane geometries.

22. The system of claim 21, wherein the membrane geometries are characterized by lateral dimensions between 5 μm and 250 μm.

23. The system of claim 21, wherein the membrane geometries are characterized by lateral dimensions between 250 μm and 1000 μm.

24. The system of claim 16, wherein the system is configured to spatially map at least one of the microbubble activity or image the body section by image reconstruction.

25. The system of claim 24, wherein the image reconstruction comprises plane wave spectrum combinations, delay and sum, phased array, synthetic aperture, and short spatial coherence.

26. The system of claim 1, wherein at least one of the CMUTs operates in a different vibrational mode from another of the CMUTs.

27. The system of claim 7, wherein the MUTAs further comprise one or more piezoelectric micromachined ultrasonic transducers (PMUTs).

* * * * *